US008444797B2

(12) United States Patent
Huang

(10) Patent No.: US 8,444,797 B2
(45) Date of Patent: May 21, 2013

(54) EARMUFF ASSEMBLY METHOD

(75) Inventor: Cherry Huang, Taipei (TW)

(73) Assignee: Thunder International Ltd., Taipei (TW)

( * ) Notice: Subject to any disclaimer, the term of this patent is extended or adjusted under 35 U.S.C. 154(b) by 344 days.

(21) Appl. No.: 13/024,334

(22) Filed: Feb. 10, 2011

(65) Prior Publication Data

US 2012/0205036 A1 Aug. 16, 2012

(51) Int. Cl.
*A61F 11/14* (2006.01)

(52) U.S. Cl.
USPC ................................ 156/212; 156/226; 2/209

(58) Field of Classification Search
None
See application file for complete search history.

(56) References Cited

U.S. PATENT DOCUMENTS

| | | | | |
|---|---|---|---|---|
| 6,724,906 | B2 * | 4/2004 | Naksen et al. | 381/379 |
| 7,853,034 | B1 * | 12/2010 | Gresko | 381/372 |
| 8,098,872 | B2 * | 1/2012 | Chang | 381/371 |
| 8,139,807 | B2 * | 3/2012 | Reiss et al. | 381/375 |

* cited by examiner

*Primary Examiner* — Barbara J Musser
(74) *Attorney, Agent, or Firm* — Leong C. Lei

(57) ABSTRACT

According to the method, a flexible pad is first adhered to a base plate, and then a front cover made of a soft material is joined to cover the flexible pad. An additional rim section from the front cover is preserved and folded inward to cover and adhere to a back wall of the base plate. Finally, a back cover with a number of magnetic elements installed is joined to the base plate so that the rim section of the front cover is locked and concealed by the back cover. As described above, an earmuff is quickly assembled and could be quickly and detachably attached to and replaced later from the headset for cleaning, greatly enhancing the usability of the headset.

8 Claims, 8 Drawing Sheets

EARMUFF ASSEMBLY METHOD

TECHNICAL FIELD OF THE INVENTION

The present invention is generally related to headset earmuffs, and more particularly to a method for assembling an earmuff capable of quickly and detachably mounting to and dismounting from a headset.

DESCRIPTION OF THE PRIOR ART

Earphones or headsets, since their origination, have been the basic accessory for various music playing appliances from radio, record player, to the latest digital players. Especially recently, as the portable appliances are all equipped with AV functions, the importance of headsets are getting even higher. For headset developers, it is vital to maintain a competitive edge in this crowded market.

Earmuffs are key components for high-end headsets. Conventionally, they are fixedly attached to a headset and cannot be replaced. If the earmuffs are damaged or broken, the usability of the headset is compromised. On the other hand, as earmuffs are in tight contact with a user's skin, the conventional fixed earmuffs cannot be removed for cleaning and then re-installed.

SUMMARY OF THE INVENTION

As such, a novel method for assembling earmuffs is provided herein. A major objective of the present invention is that the earmuffs could be easily assembled without the use of bolts and nuts and therefore so as to achieve high production efficiency and quantity.

Another objective of the present invention is that the earmuffs could be conveniently and dynamically joined to and removed from a headset, so as to enhance the competitiveness of the headset.

To achieve the foregoing objectives, the present invention contains the following steps.

Firstly, a flexible pad is adhered to a base plate. The base plate has a first through opening in the middle, a number of through holes around the first through opening, and a back wall extended backward around the circumference of the base plate. Adhesive is applied on a front side of the base plate, and then aligning and attaching the flexible pad to the front side of the base plate. The flexible pad is shaped substantially identical to the base plate and also has a second through opening in the middle.

Secondly, a front cover is joined to the flexible pad by die pressing an appropriately cut material for the front cover completely over the flexible pad. An additional rim section is preserved and folded inward to cover and adhere to the back wall.

Finally, a back cover with a number of magnetic elements installed is joined to the base plate. The back cover is also shaped substantially identical to the base plate and also has a third through opening in the middle. Corresponding to the through holes, the back cover is configured with a number of locking pins whose back ends are configured with indentations for the installation of the magnetic elements. The back cover is tightly attached to the base plate and the rim section of the front cover is locked and concealed by the back cover.

As described above, an earmuff is quickly assembled and could be quickly attached to and replaced later from a headset for cleaning, greatly enhancing the usability of the headset.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
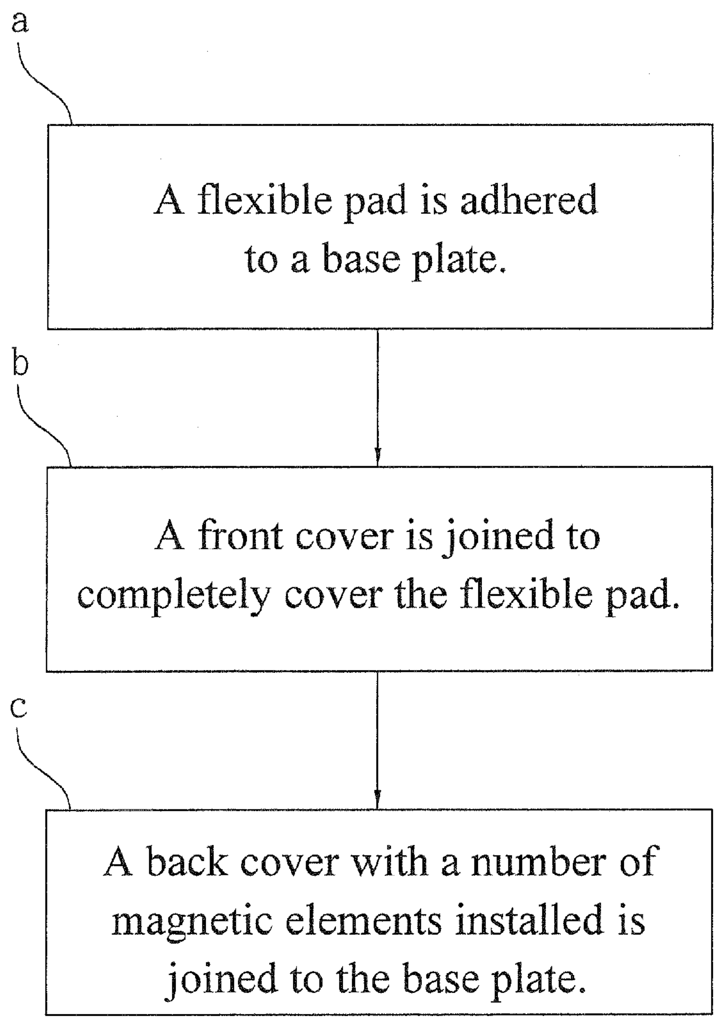
FIG. 1 is a flow diagram showing the steps according to an embodiment of the present invention.
Figure 2:
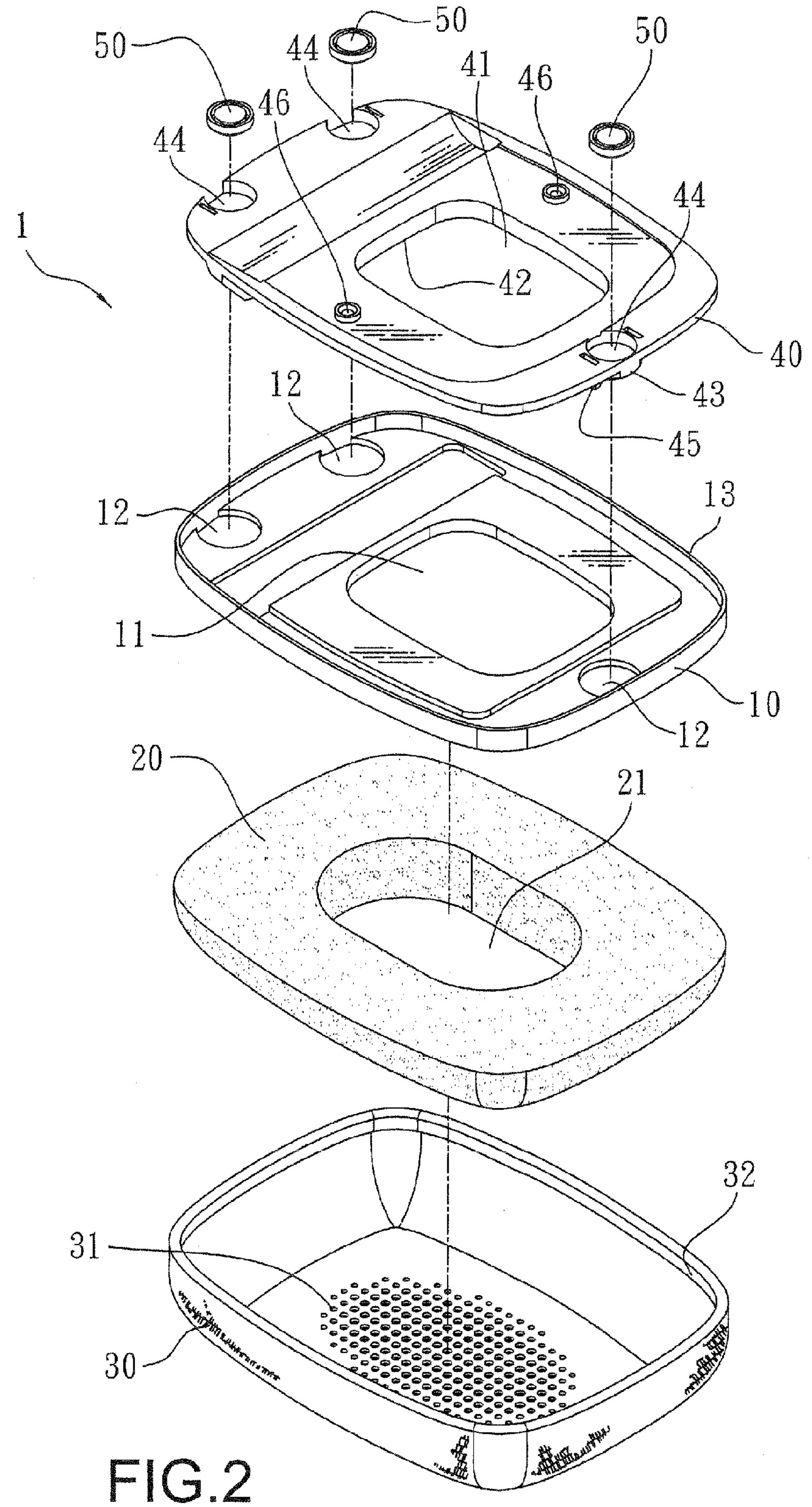
FIG. 2 is a perspective break-down diagram showing the various components of an earmuff assembled by the method of FIG. 1.
Figure 9:
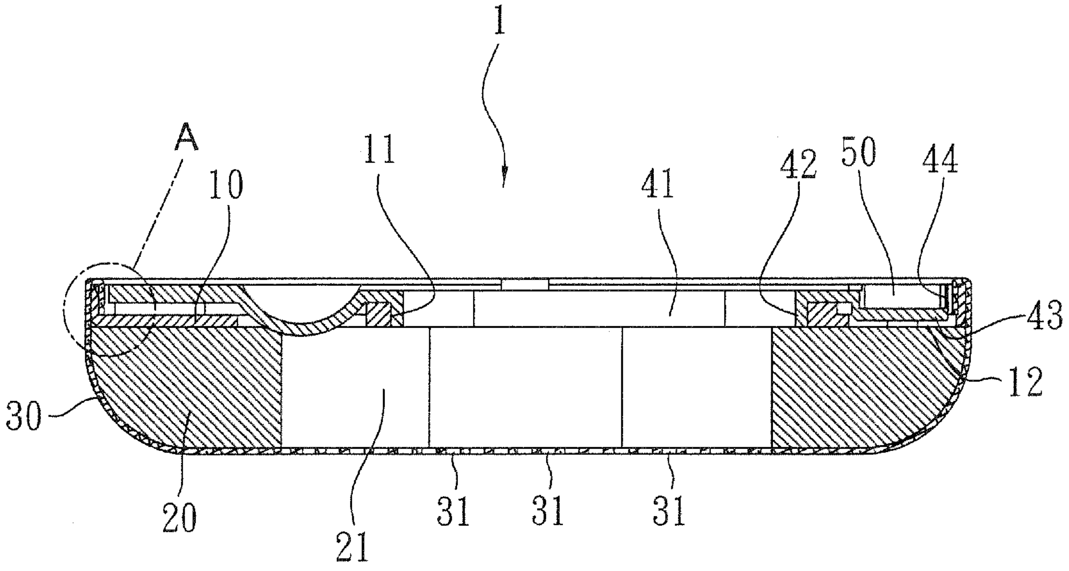
FIG. 9 is a schematic sectional diagram showing the earmuff of FIG. 2.

As shown in FIGS. 2 and 9, an earmuff 1 assembled by the present invention mainly contains a base plate 10, a flexible pad 20, a front cover 30, a back cover 40, and a number of magnetic elements 50.

The base plate 10 has a first through opening 11 in the middle and a number of through holes 12. Additionally, a back wall 13 is extended backward around the circumference of the base plate 10.

The flexible pad 20 is shaped substantially identical to the base plate 10 and also has a second through opening 21 in the middle.

The front cover 30 is made of a soft material such as leather or cloth and is configured with a number of sound holes 31 gathered substantially in the middle.

The back cover 40 is also shaped substantially identical to the base plate 10 and also has a third through opening 41 in the middle. A front wall 42 is extended forward around the circumference of the third through opening 41, through which the back cover 40 could be quickly snapped to the base plate 10 by embedding the front wall 42 into the first through opening 11. Corresponding to the through holes 12 in terms of their shapes and positions, the back cover 40 is configured with a number of locking pins 43. Due to the front wall 42, the back wall 13, the locking pins 43, and the through holes 12, the back cover 40 is tightly attached to the base plate 10 and lossless sound delivery is guaranteed as air is prevented from between the base plate 10 and the back cover 40. Each pin 43's back end is configured with an indentation 44 for the installation of a magnetic element 50. Optionally, a number of positioning holes 46 are configured on a back side of the back cover 40, and hook elements 45 are configured on a front side of the back cover 40 adjacent to the locking pins 43.

As shown in FIGS. 1, and 3 to 9, the earmuff assembly method according to an embodiment of the present invention contains the following steps.

Figure 3:
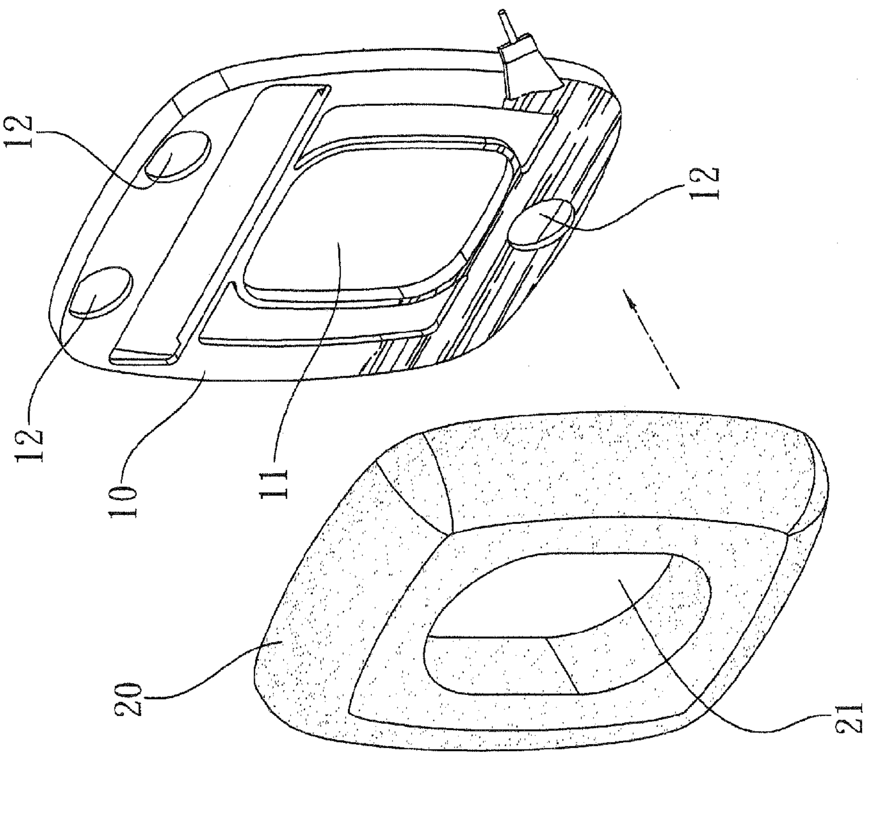
FIG. 3 is a perspective diagram showing a scenario of the first step of the method of FIG. 1.

Firstly, as shown in FIG. 3, the flexible pad 20 is adhered to the base plate 10 by applying adhesive on a front side of the base plate 10, and then aligning and attaching the flexible pad 20 to the front side of the base plate 10.

Figure 4:
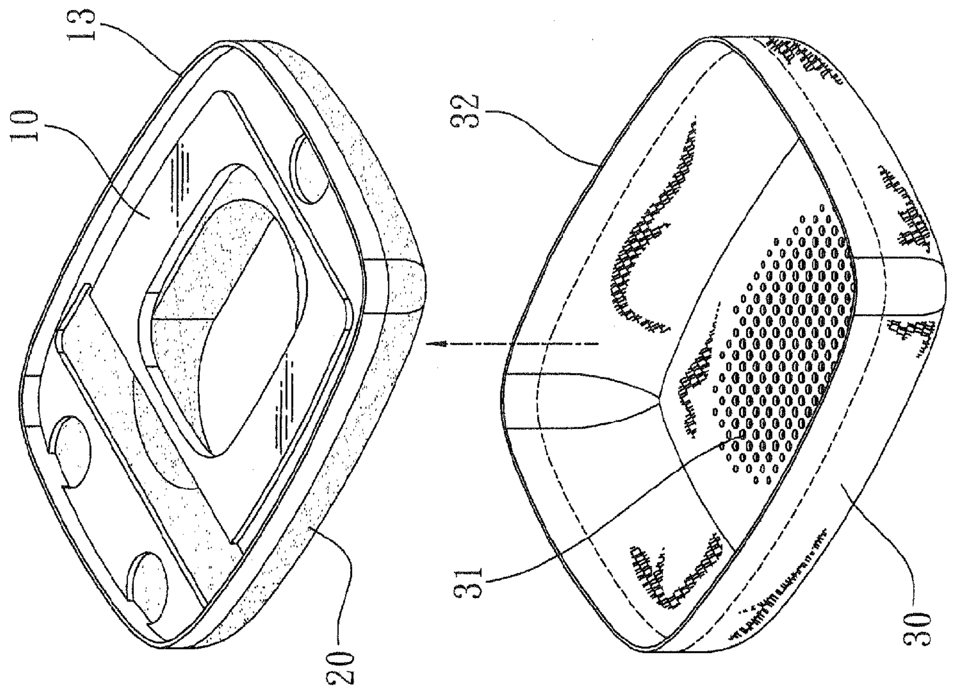
FIGS. 4 and 5 are perspective diagrams showing scenarios of the second step of the method of FIG. 1.
Figure 5:
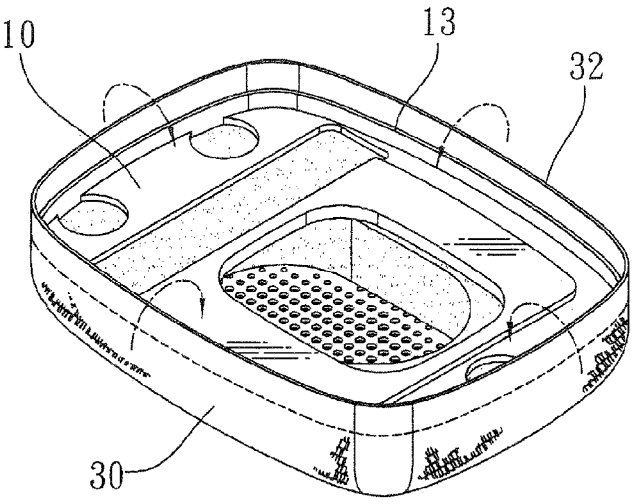
Figure 6:
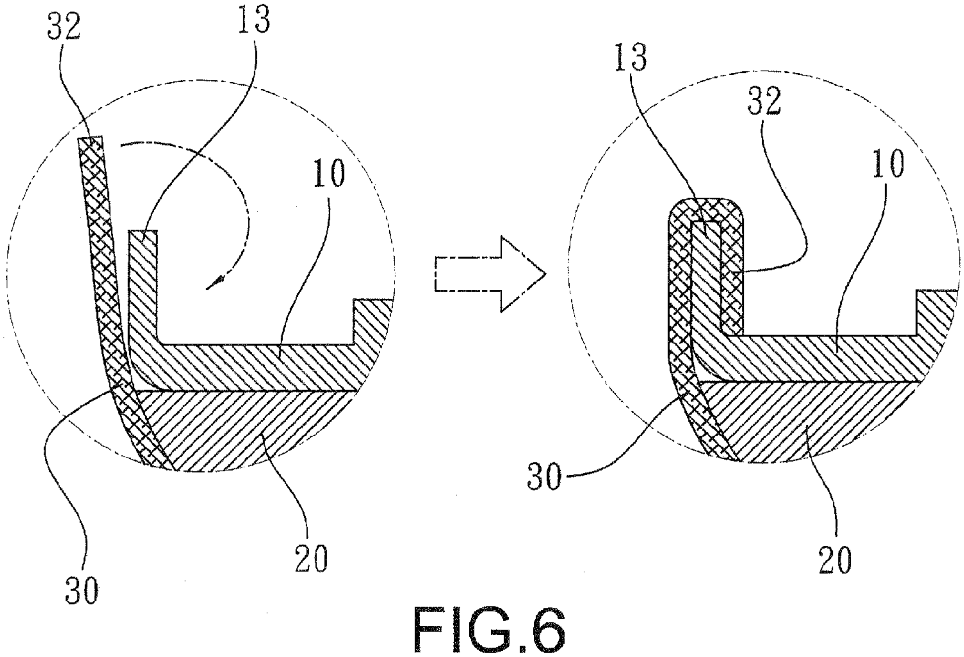
FIG. 6 is a schematic sectional diagram showing a detailed scenario of the second step of the method of FIG. 1.

Secondly, as shown in FIGS. 4 and 5, the front cover 30 is joined to the flexible pad 20 by die pressing an appropriately cut material for the front cover 30 completely over the flexible pad 20. As more clearly shown in FIG. 6, the material for the front cover 30 is cut so that an additional rim section 32 is preserved. Then, the back wall 13's inner surface is applied with adhesive and the rim section 32 is folded inward to cover and attach to the back wall 13.

Figure 7:
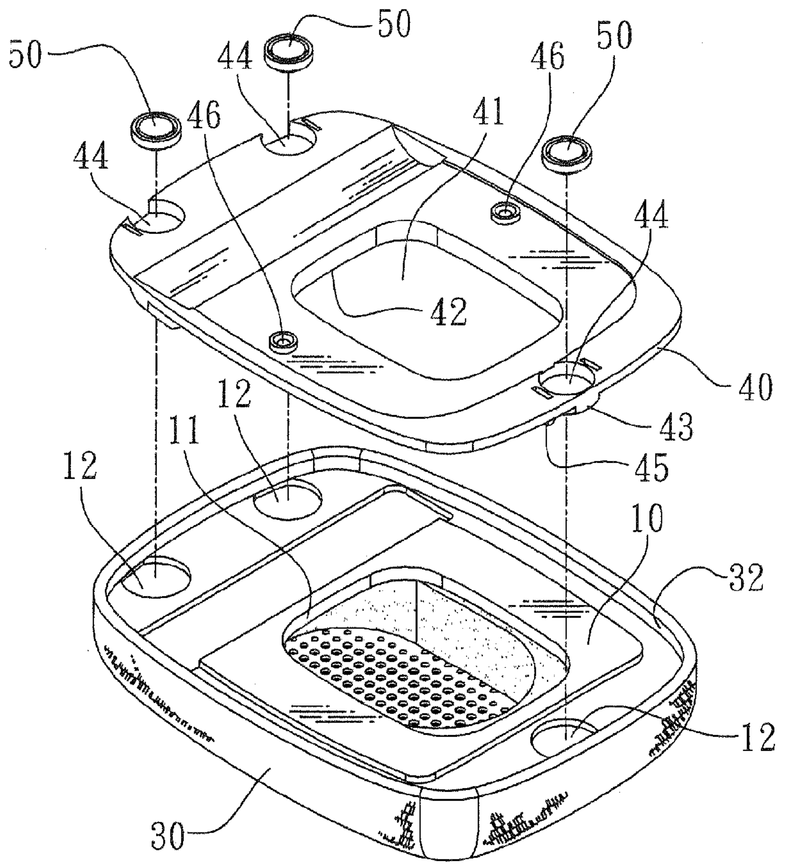
FIGS. 7 and 8 are perspective diagrams showing scenarios of the third step of the method of FIG. 1.
Figure 8:
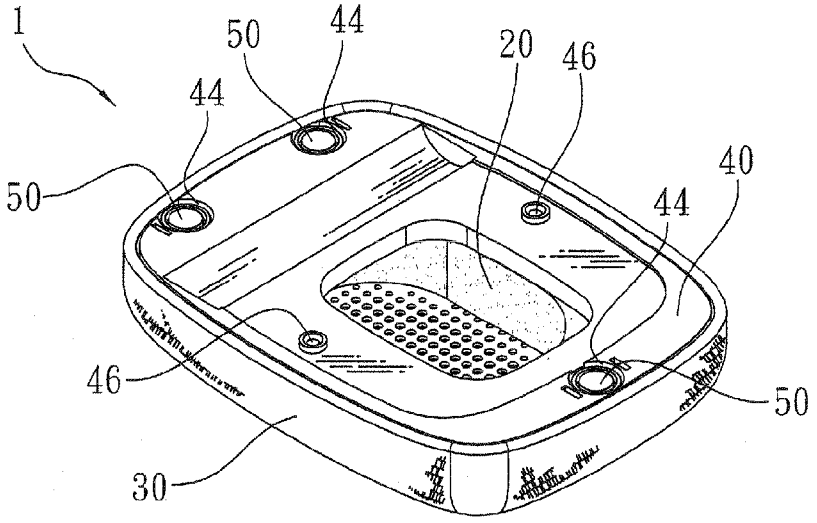
Figure 9A:
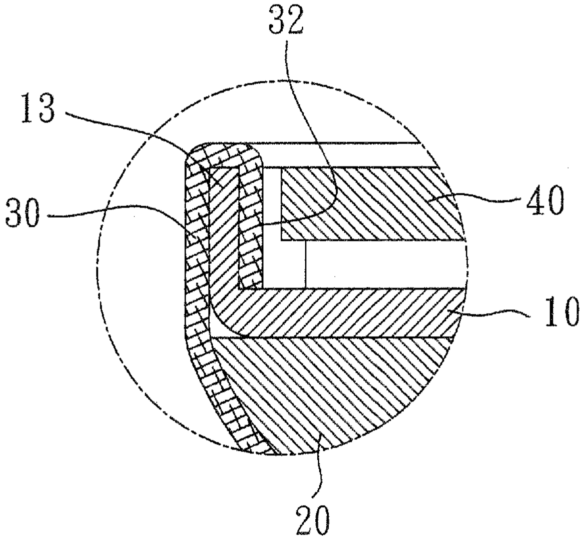
FIG. 9A is a schematic sectional diagram showing an enlarged section of FIG. 9.

Finally, as shown in FIGS. 7 and 8, the back cover 40 with the magnetic elements 50 installed is joined to the base plate 10 by applying adhesive or two-sides adhesive tape to the back side the base plate 10, and then attaching the back cover 40 to the base plate 10 by aligning the front wall 42 and the locking pins 43 to the first through opening 11 and the through holes 12, respectively. The hook elements 45 could further lock the rims of the through holes 12, to enhance the reliability of the back cover 40's joining to the base plate 10. The rim section 32 is as such further locked and concealed by the back cover 40 as shown in FIGS. 9 and 9A. Alternatively, the magnetic elements 50 could be installed after the back cover 40 is joined to the base plate 10. As described above, the entire assembly process does not require any bolt and nut.

Figure 10:
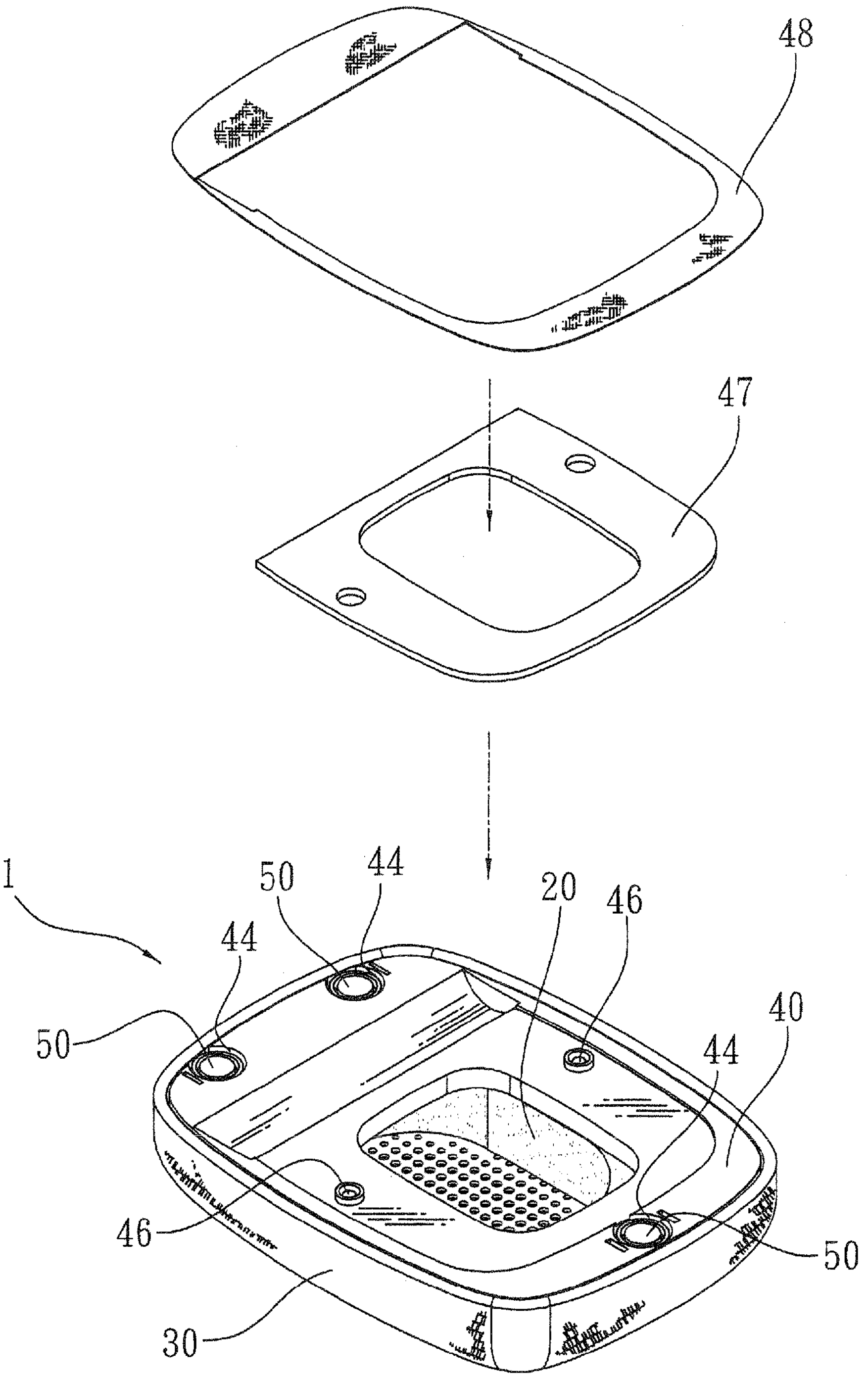
FIGS. 10 and 11 are perspective diagrams showing scenarios of attaching a cushion piece and a cloth piece to the earmuff.
Figure 11:
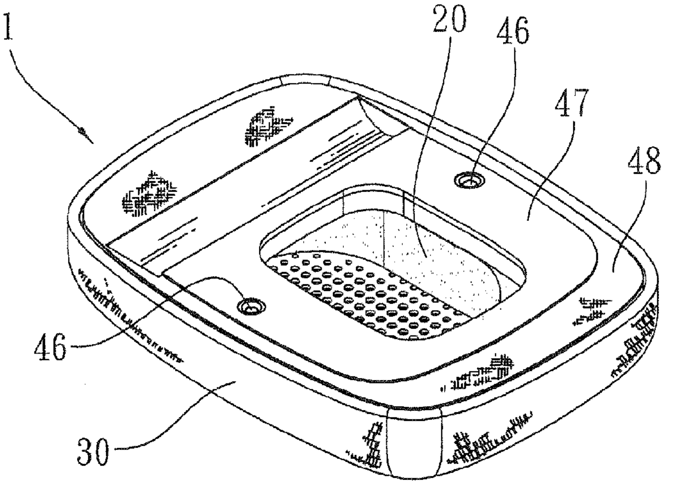
Figure 12:
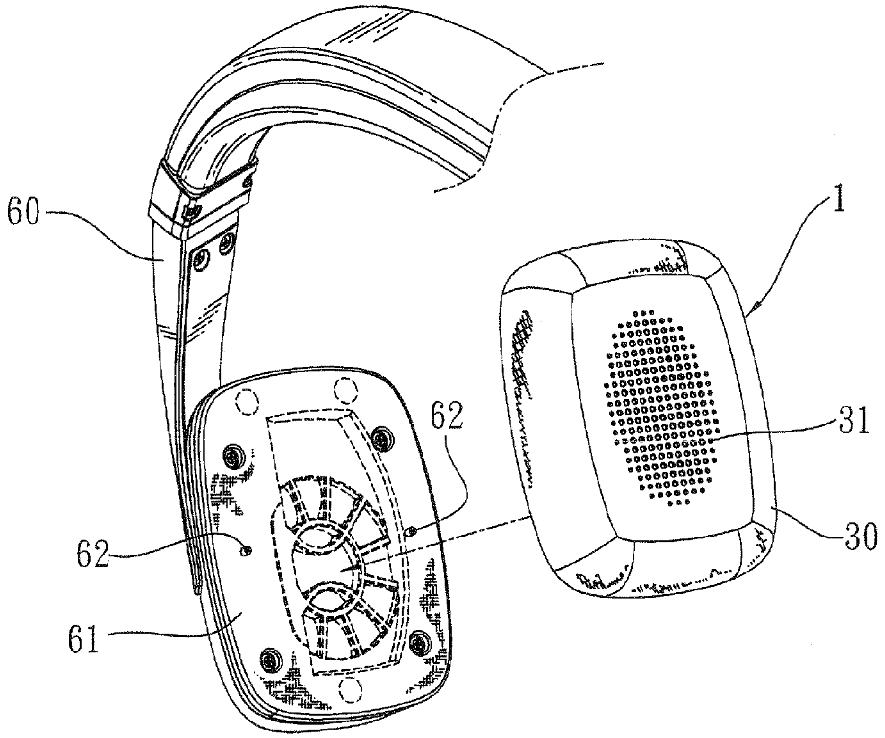
FIG. 12 is a perspective diagram showing an scenario of joining a earmuff assembled by the present invention to a headset.

As shown in FIGS. 10 to 12, a cushion piece 47 made of polymer foam could be further configured around the third through opening 41 so as to prevent any air gap that would cause deteriorated sound quality between the earmuff 1 and a headset 60 when the former is joined to the latter. Further, a non-woven cloth piece 48 is applied to cover the magnetic elements 50 and to enhance the earmuff 1's appearance. The magnetic elements 50 are high-performance magnets wrapped by steel casings so as to prevent the leakage of magnetic flux. To join the earmuff 1 to the headset 60, the positioning holes 46 are aligned with a number of positioning pins 62 on an ear piece 61 of the headset, and then the earmuff 1 is automatically attracted to the ear piece 61.

The advantage of the present invention is as follows.

Firstly, due to its simplified structure and easy assembly, the production performance of the earmuff is significantly enhanced.

Secondly, the earmuff 1 has enhanced look and feel so that its market value is greatly increased.

Thirdly, the earmuff 1 could be conveniently replaced, contributing to the headset 60's usability and life span.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An earmuff assembly method, comprising the steps of:

adhering a flexible pad to a base plate wherein said base plate has a first through opening in the middle, a plurality of through holes around said first through opening, and a back wall extended backward around the circumference of said base plate; said flexible pad is shaped substantially identical to said base plate and also has a second through opening in the middle; adhesive is applied on a front side of said base plate; and said flexible pad is aligned and attached to said front side of said base plate;

joining a front cover to said flexible pad by die pressing an appropriately cut material for said front cover completely over said flexible pad wherein an additional rim section is preserved and folded inward to cover and adhere to said back wall; and joining a back cover with a plurality of magnetic elements installed to a back side of said base plate wherein said back cover is also shaped substantially identical to said base plate and also has a third through opening in the middle; corresponding to said through holes, said back cover is configured with a plurality of locking pins whose back ends are configured with indentations for the installation of said magnetic elements; said back cover is tightly attached to said base plate and said rim section of said front cover is locked and concealed by said back cover.

2. The earmuff assembly method according to claim 1, wherein said material for said front cover is one of leather and cloth.

3. The earmuff assembly method according to claim 1, wherein a front wall is extended forward around the circumference of said third through opening, through which said back cover is joined to said base plate by embedding said front wall into said first through opening.

4. The earmuff assembly method according to claim 1, wherein a plurality of hook elements are configured on a front side of said back cover adjacent to said locking pins.

5. The earmuff assembly method according to claim 1, wherein a plurality of positioning holes are configured on said back cover.

6. The earmuff assembly method according to claim 1, wherein said magnetic elements are high-performance magnets wrapped in steel casings.

7. The earmuff assembly method according to claim 1, further comprising the step of:

attaching a cushion piece to a back side of said back cover around said third through opening.

8. The earmuff assembly method according to claim 1, further comprising the step of:

attaching a non-woven cloth piece to a back side of said back cover over said magnetic elements.

* * * * *